US012594693B2

(12) United States Patent
Menneglier

(10) Patent No.: US 12,594,693 B2
(45) Date of Patent: Apr. 7, 2026

(54) METHOD AND DEVICE FOR RECYCLING ROPES

(71) Applicant: Jean-Mathieu Menneglier, Mareil-Marly (FR)

(72) Inventor: Jean-Mathieu Menneglier, Mareil-Marly (FR)

(73) Assignee: Jean-Mathieu Menneglier, Mareil-Marly (FR)

( * ) Notice: Subject to any disclaimer, the term of this patent is extended or adjusted under 35 U.S.C. 154(b) by 1182 days.

(21) Appl. No.: 17/438,215

(22) PCT Filed: Mar. 13, 2020

(86) PCT No.: PCT/EP2020/056985
§ 371 (c)(1),
(2) Date: Sep. 10, 2021

(87) PCT Pub. No.: WO2020/183018
PCT Pub. Date: Sep. 17, 2020

(65) Prior Publication Data
US 2022/0212370 A1 Jul. 7, 2022

(30) Foreign Application Priority Data
Mar. 13, 2019 (FR) ...................................... 1902553

(51) Int. Cl.
B29B 17/00 (2006.01)
B29B 17/02 (2006.01)
(Continued)

(52) U.S. Cl.
CPC .............. *B29B 17/02* (2013.01); *B29B 17/04* (2013.01); *C12N 1/12* (2013.01); *C12N 9/00* (2013.01);
(Continued)

(58) Field of Classification Search
CPC ...................... B29B 2017/0203; Y02W 30/66
See application file for complete search history.

(56) References Cited

U.S. PATENT DOCUMENTS

2010/0267868 A1* 10/2010 Takahashi ............... B29B 17/02
524/79
2019/0217504 A1* 7/2019 Wang ...................... B29B 17/04
2020/0299869 A1* 9/2020 Gallo ...................... B29B 17/02

FOREIGN PATENT DOCUMENTS

BE 445393 A 6/1942
CN 107738382 A 2/2018
(Continued)

OTHER PUBLICATIONS

English translation of FR 3007412 (generated 2025).*
(Continued)

*Primary Examiner* — Nathan A Bowers
(74) *Attorney, Agent, or Firm* — Affordable Patent Agency; Bela Malik

(57) ABSTRACT
Method for recycling composite ropes, the method comprising a step of identifying (SO) the type of rope and at least one step of separating components comprising one or the other of the following steps /S1/, /S2/, /S3/, /S4/ as defined below: /SI/—a mechanical separation step, /S2/—a chemical separation step, /S3/—a thermal separation step, /S4/—a biological separation step and machine or installation for recycling composite ropes.

20 Claims, 4 Drawing Sheets

(51) Int. Cl.
  *B29B 17/04*       (2006.01)
  *C12N 1/12*        (2006.01)
  *C12N 9/00*        (2006.01)

(52) U.S. Cl.
  CPC ................. *B29B 2017/0203* (2013.01); *B29B*
            *2017/0217* (2013.01); *B29B 2017/0255*
        (2013.01); *B29B 2017/0279* (2013.01); *B29B*
                         *2017/0293* (2013.01)

(56)           References Cited

FOREIGN PATENT DOCUMENTS

| | | | |
|---|---|---|---|
| DE | 19507513 | A1 | 9/1996 |
| DE | 102013200482 | A1 | 7/2014 |
| FR | 3007412 | A1 | 12/2014 |
| WO | WO-2013050942 | A1 * | 4/2013 |
| WO | WO-2016198781 | A1 * | 12/2016 |

OTHER PUBLICATIONS

PCT International Search Report and Written Opinion in PCT/
EP2020/056985 dated May 26, 2020, 11 pages.
Korzen, Z., "Recovery of Rubber and Steel Cords From Conveyor
Belts", International Polymer Science and Technology, Rapra Tech-
nology, Shrewabury, GB, vol. 19, No. 12, Jan. 1, 1992 (Jan. 1,
1992), pp. T51-T57.

* cited by examiner

FIG. 3
36
37
2
21
22
FIG. 4
46
44
47
48
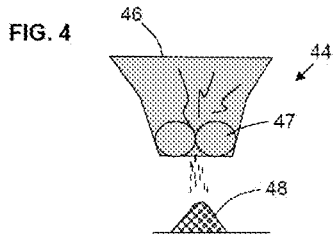
FIG. 5
53
54
55
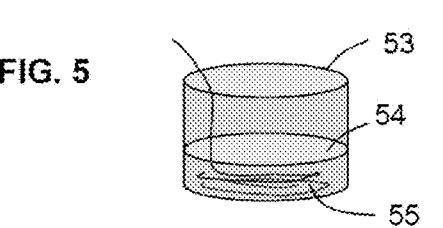

METHOD AND DEVICE FOR RECYCLING ROPES

CROSS REFERENCE TO RELATED APPLICATIONS

This is a National Phase entry of International Application No. PCT/EP2020/056985, filed Mar. 13, 2020, which claims priority to French Patent Application No. FR1902553, filed Mar. 13, 2019, the disclosures of which are incorporated herein by reference in their entireties.

TECHNICAL FIELD

The invention relates to methods and devices for recycling strings. We are particularly interested in the recycling of sports racket strings. However, the invention is also aimed at recycling technical strings such as those used for sailing, rock climbing, mountaineering or even other sports. It is also considered that the present invention can be applied to the strings of musical instruments, in particular stringed instruments.

BACKGROUND AND PRIOR ART

Currently, broken or used strings from sports racquets (tennis, squash, badminton) are thrown in the trash or thrown away carelessly.

As long as, in a previous situation, the strings were obtained from natural fibers of animal or plant origin, they could be considered as naturally bio-degradable materials and their landfill or even their rejection in any such place was not a problem from an environmental point of view.

However, it turns out that, in more and more cases, these strings include synthetic components and technical fibers which are not directly biodegradable. Disposing of them in the trash, therefore, has a negative ecological impact on the environment. Some components can be considered toxic waste.

There is pressure from public authorities and non-governmental organizations to manage waste linked to human activity and achieve a real circular economy and very high recycling rates.

The present invention provides a solution whereby many strings can be recycled.

SUMMARY OF THE INVENTION

To this end, a process for recycling composite strings is proposed, with the process comprising:

a step of identifying the type of string, and at least one step of separating components comprising one or the other of the following steps /S1/, /S2/, /S3/, /S4/ as defined below:

/S1/—a mechanical separation step,
/S2/—a chemical separation step,
/S3/—a thermal separation step,
/S4/—a biological separation step.

Following these steps, it is possible to advantageously recycle strings, in particular, the strings of sports rackets, and thus avoid throwing them in the trash.

This method makes it possible to set up a "green circular economy" around the processing of strings, in particular racket strings. The circular economy will make it possible to use polluting waste by transforming its composition into a recoverable resource.

Depending on its composition, each component of the string is converted by reintroducing it into a new production cycle.

Thus, a solution is proposed making it possible to not throw strings into the residual household waste, so that the latter is no longer discarded, but recovered; thanks to technical solutions for local recycling or recovered collected waste.

In various embodiments of the invention relating to the system, one and/or the other of the following arrangements, taken alone or in combination, may also optionally be used.

According to an embodiment of interest, the strings to be recycled are strings for sports rackets with strings. We include in sports equipment with strings, in particular but not exclusively, tennis, badminton, squash.

According to another embodiment, the proposed method may be used for technical strings used for sailing, rock climbing, mountaineering or other sports. According to another embodiment, the proposed method may be used for the strings of musical instruments, in particular stringed instruments such as violin, cello, guitar, double bass.

According to one embodiment of interest, the strings to be recycled are tennis racket strings. This inventor has discovered that, for tennis racket strings, there are increasingly greater amounts of composite strings.

On the other hand, both for professional players and for seasoned amateur players, said players tend to replace the string before it breaks or reaches its real end of life, which considerably increases the quantities consumed and makes the proposed recycling solution even more attractive.

According to one option, the tennis racket strings comprise an assembly of structural fibers with a coating material, the structural fibers comprising aramid and/or polyester and/or polyamide fibers and/or polyolefin and/or polyethylene, and the coating material comprising polyurethane and/or an elastomer. The proposed process thus makes it possible to process a very wide variety of types of technical strings for tennis or strings for other uses. Most of the usual components in terms of fibers are thus included and a very high recyclability rate can be achieved.

According to one embodiment, for the step of mechanical separation (S1) of the fibers and the coating, a step of peeling and/or a step of grinding the cord strand is provided. Whereby, when the length of the strings to be processed allows it, the string can be passed through a machine similar to an extruder in which graters peel the coating material, at least for its outer edges. As for the grinding step, the latter allows the string strand to be cut into small pieces which can then be processed by a chemical, thermal or biological separation step.

According to one embodiment, for the chemical separation step, dissolution of the coating of the fibers in a solvent can be specified. As a result, it is possible to completely and reliably separate the technical fibers from the coating material.

According to one embodiment, the thermal separation step can include a vapor-thermolysis step, with heating of the cord strand above 150°. Whereby, depending on the melting points of the different components, it is possible to progressively separate, by increasing the temperature and recovering the components which have the lowest melting point first, and later, the components which have the highest melting point.

According to another embodiment, the biological separation step comprises the extended placing of the cordage strands in contact with active biological agents comprising microalgae and/or enzymes, so that certain components of the cordage strands which are of interest are degraded by said active biological agents. Such that, even if the time required is longer, this solution is the most economical in energy to achieve the separation of the components.

According to another embodiment, such a biological separation step can be used to process natural gut strings by recycling. Active biological agents comprising microalgae and/or enzymes degrade natural gut strings into elementary chemical components, which then no longer have any problematic impact on the environment.

According to one embodiment, the identification step for tennis racket strings is to make a cross section, take a photo with magnification, and analyze the groups of filaments, to derive a classification among at least the following types: single multi filaments, multi core multi filaments, multi core multi sheath, multi core single sheath. Whereby, one can then choose, depending on the identification obtained, the most appropriate separation step(s).

According to one embodiment, the cross section obtained can be compared with reference sections, as one example, from a Smartphone® application.

The present invention also relates to a machine for recycling composite strings, in particular tennis racket strings, characterized in that it is configured to implement, in part or in whole, the method described above.

BRIEF DESCRIPTION OF THE DRAWINGS

Other aspects, aims and advantages of the invention will become apparent on reading the following description of an embodiment of the invention, given by way of non-limiting example. The invention will also be better understood in relation to the accompanying drawings in which:

FIG. 3 shows a step of mechanical separation by peeling,

FIG. 4 illustrates a mechanical separation step by grinding,

FIG. 5 illustrates a chemical separation step,

DESCRIPTION OF EMBODIMENTS

In the various figures, the same references designate identical or similar elements. For reasons of clarity of the presentation, certain elements are not necessarily represented to scale.

Figure 1:
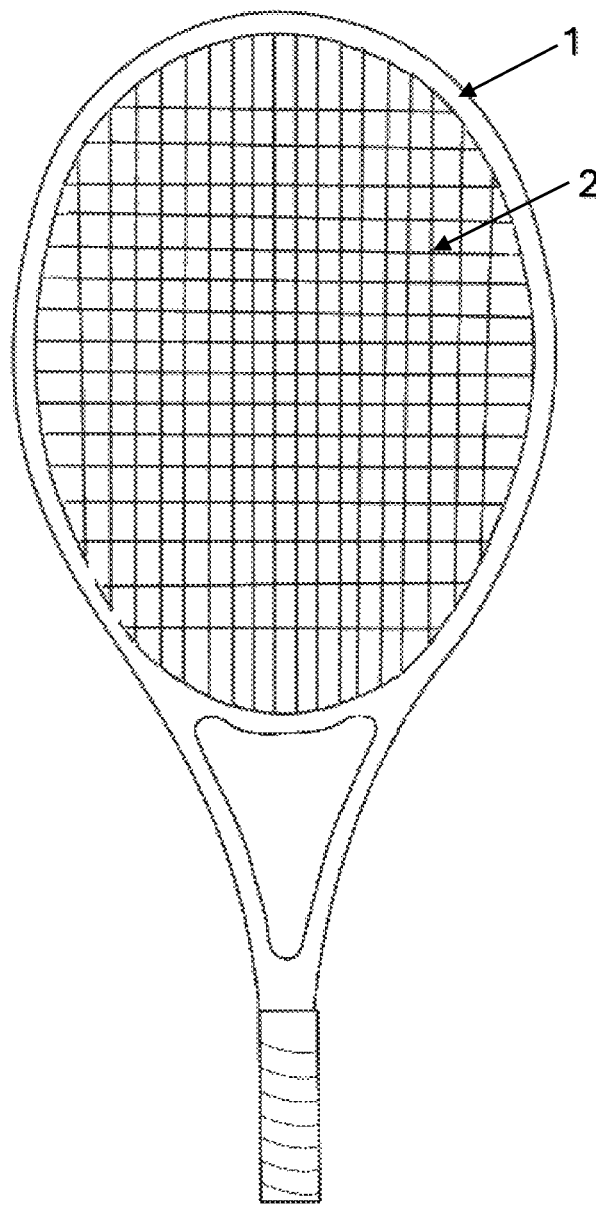
FIG. 1 shows an illustration of a tennis racket with its string.

FIG. 1 partially shows a tennis racket with its string. The racket comprises a frame 1 and string 2. The string passes through holes made in the frame. The string forms a sieve. Longitudinal sections intersect cross sections. To complete the operation of installing the string, several knots are created.

String 2 can break after some wear, or if the stress endured exceeds the threshold that can be tolerated by the type of string in question. Some users or players replace the string preventively as already mentioned.

To remove the string from the frame, the string threads can be removed through the holes in the frame, after sectioning the string several times.

We are interested in the very frequent case where the string 2 itself is formed from an assembly of structural fibers with a coating material. When we talk in more detail about the composition of the string, we can also use the term "string strand" to denote a single element of the whole string. The string strand may in some cases include a solid core 32.

Of particular interest are string strands having an outside diameter of between 0.8 mm and 1.6 mm. According to the example, in particular, string threads having an outer diameter of between 1 mm and 1.5 mm are processed.

With regard to string strands for tennis rackets, the cross section of the strand has a diameter of between 1.2 mm and 1.4 mm. However, note that smaller to larger diameters are also considered in the method of the present invention.

The coating material, marked 4, comprises polyurethane and/or an elastomer. Note that to designate "coating", we also speak of "sheathing". The tensile strength mechanical pstringrty of the coating material string is less than that of structural fibers; but the coating material does contribute to the cohesion of the string strand.

Figure 2:
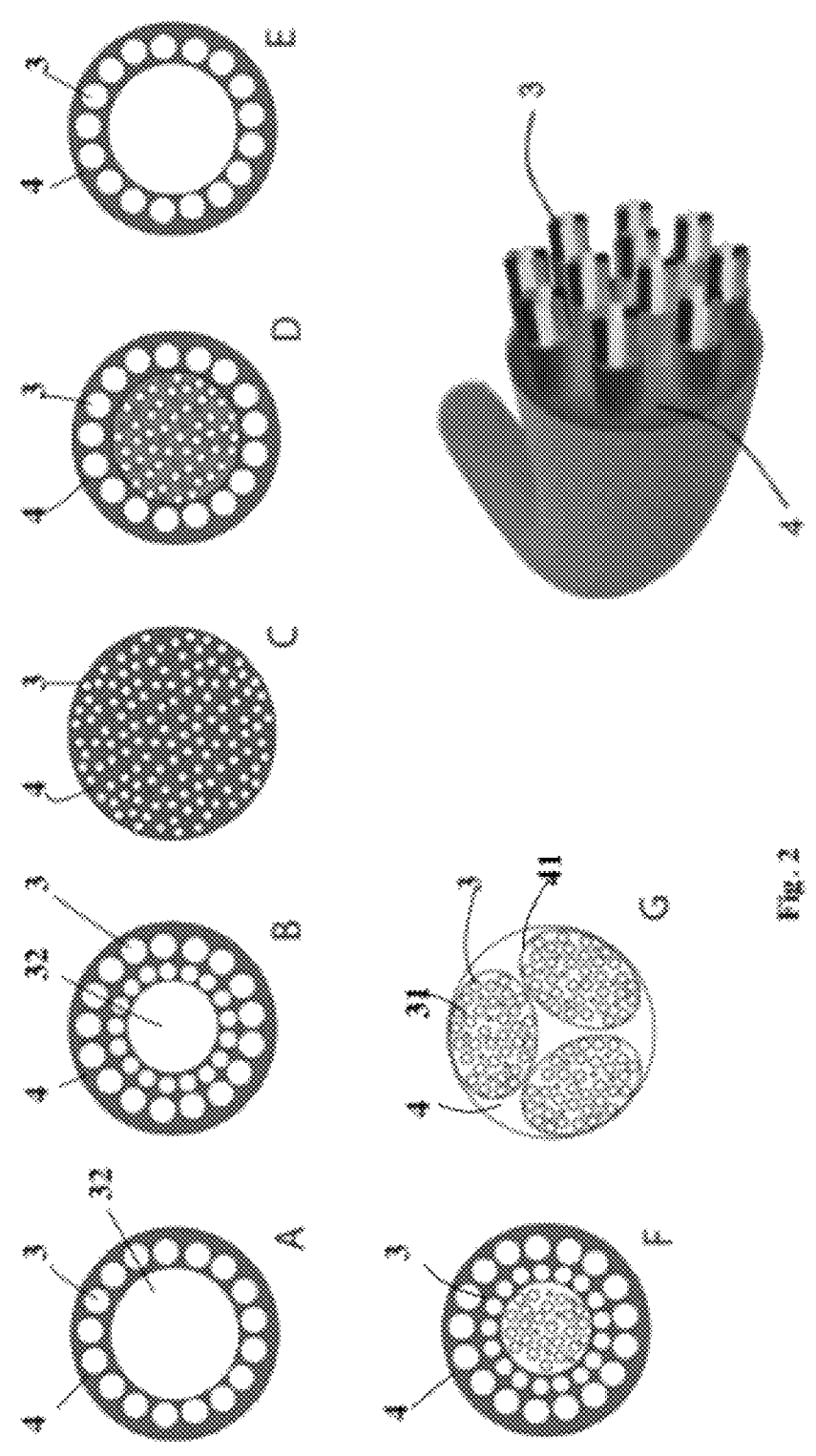
FIG. 2 illustrates several types of strings sections to be recycled.

As illustrated in FIG. 2, the structure of the string strand can be of several types: single multifilament, multicore multifilament, multicore multi sheath, multi core single sheath.

FIG. 2, example A: solid core, 1 sheathing

FIG. 2, example B: solid core, multi-sheath

FIG. 2, example C: multifilament, coreless

FIG. 2, example D: solid multi-core, 1 sheath

FIG. 2, example E: solid multi-core, 1 sheath

FIG. 2, example F: multi-core, multi-duct

FIG. 2, example G: multi-core, multi-duct

The structural fibers, generally denoted 3 in the figures, comprise aramid and/or polyester and/or polyamide and/or polyolefin and/or polyethylene fibers.

The structural fibers used for tennis strings or for other types of strings (see list above) include in particular:

Aramid: Zylon (PBO); Kevlar (PPD-T); Kevlar 49; Black Technora,

Polyester: Pen or Pentex (PEN); Polyester (PES), Polyamide: Nylon; Polyamide,

Polyolefins: Spectra or Dyneema; HDPE polyethylene,

Titanium: Titanium (Ti),

Carbon: Carbon fibers,

Elastomer: Polybutylene; elastomers (rubbers).

Aramids

Aramid fibers are recognized for their excellent impact resistance, and are widely used in the manufacture of personal protective equipment (helmets, cut resistant gloves, bulletproof vests, etc.). In boating, Kevlar® or Technora® products are appreciated for their very good strength and low elongation at break (around 3.5%), as well as their remarkable stability under static load (no creep). In other words, these fibers are very strong (five times more so than stainless steel), very weakly elastic and do not stretch over time.

Aramid fibers are also used as reinforcements in composite materials, in order to provide good temperature stability to the end products (up to 200° C. depending on the matrix). However, we can note some less positive points: limited resistance to UV and significant cost.

Polyesters

Polyester fibers are consumer fibers known for their longevity, UV resistance and excellent mechanical and chemical resistance.

Polyester fiber can be recycled mechanically or chemically, each method having certain advantages and disadvantages. The mechanical method involves collecting plastic bottles and industrial waste, while the chemical process reuses textile products made from polyester to reduce them to monomers and then transform them back into textiles.

The polyester recycling method allows materials to be recreated almost indefinitely: items or fabrics can be recycled many times without losing quality. In addition, chemically produced recycled polyester does not contain heavy metals, unlike its counterpart made with freshly extracted petroleum.

Polyamides

Polyamide or nylon fiber is a so-called "technical" synthetic fiber. It is used in textile and plastic industrial applications, and finds application in a wide range of products requiring high strength materials. Polyamide is widely used for gears, fittings and bearings, in the automotive industry for underlying parts, and as a material for power tool housings. It is also used in the manufacture of a wide variety of strands, strings, filaments, netting and tire cords, as well as hosiery and knitted garments.

There are a wide variety and many grades of types of polyamides available industrially, known by the acronyms 'PAx.x'.

The main strengths of polyamide are its very good mechanical properties (traction, fatigue, impact, abrasion resistance), as well as good resistance to fuels and oils. On the other hand, it is sensitive to humidity in the ambient air, and has fairly limited UV resistance. Despite everything, polyamides exhibit an excellent cost/performance balance.

Polyamides are currently very infrequently recycled, for reasons related to the chemistry of the polymers (nylon is more difficult to recycle than polyester).

Polyolefins

Polyethylenes, from the polyolefin family, are part of the so-called "mass market" plastics, with very high consumption. They are one of the plastics that lend themselves to recycling, although they are often destined for low value-added applications. They are subdivided into many subcategories, each with specific characteristics (PEHD, PEBD, PEBDL, UWMWPE . . . ).

High tenacity polyethylene fibers (commonly called "Ultra-High Molecular Weight Polyethylene", or UHMWPE) have the advantages of lightness (density of 0.95 compared to that of aramid of 1.44) and with a high capacity for converting kinetic energy into thermal energy. They are increasingly used in bulletproof vests and other ballistic applications, in competition with Kevlar, to reduce weight.

The polyethylene fibers of the Dyneema™ range (from the manufacturer DSM) and Spectra™ (from the manufacturer Honeywell) are characterized by their very high resistance, and this for a minimum weight. Indeed, for equal weight, such a fiber is up to 15 times stronger than high-grade steel and 40% stronger than an aramid fiber. In addition, these fibers are lighter than water, extremely durable and resistant to mold, UV rays and chemicals.

As for the drawbacks, it should be noted a poor resistance to temperature (creep from 90° C.; aramid only degrades at 400° C.), as well as poor adhesion pstringrties which make composite applications delicate (surface treatment required).

Titanium

Titanium is a light and resistant metal, considered "noble". It exhibits interesting industrial properties such as its resistance to corrosion, erosion and fire. It is ductile and biocompatible and also exhibits mechanical properties which allow the shaping of thin and light parts.

Because of its many qualities, it is used in many areas with high added value: medical, aeronautics, petrochemicals and new mechanical and leisure sports, where weight reduction becomes a gauge of performance. Titanium is a metal which combines very interesting mechanical qualities and excellent resistance in corrosive environments, which makes surface treatments unnecessary and makes titanium "ecological". In addition, its density is 2 times lower than that of steels.

Titanium is mainly used in the form of alloys in aeronautics and for many industrial applications (energy, chemicals, etc.). Given the large part of production waste, the recycling of chips is well organized to recover as much material as possible. It is not uncommon to see that machining chips can represent up to 90% of titanium consumption in the production of a part. These chips are used as by-products, as in the case of the structural fibers of strings.

Carbon

Carbon fibers come from petroleum and exhibit extremely interesting properties: unfailing rigidity and mechanical stability, ultra-light weight and insensitivity to UV rays. Provided it is not exposed to impact, the life of carbon fiber is virtually unlimited.

Carbon fibers are now found in many advanced technical applications, where mechanical resistance, combined with a very low density are good assets: sports equipment, automobiles, aeronautics, robotics, military equipment, helicopter propellers, wind turbines, drones.

One of the most suitable technologies for recycling carbon fibers is pyrolysis. The material is subjected to a high temperature (between 400° C. and 700° C.), in order to lead to a degradation of the resin and a separation of the constituents. Solid or gaseous residues are thus obtained, depending on the conditions, which can be used as fuels (energy recovery, see below). The fibers can be recovered at the end of the process to be reintroduced into plastics or composites. The main advantage of this technique is the preservation of the mechanical properties of the recycled carbon fibers.

Method

After collection, the recycling process begins with an identification step (denoted S0) of strings. For tennis racket strings in particular, the identification step consists in making a transverse cut (by chisel, cutter or other sharp tool) after which a photo is taken with magnification, for example using a smartphone or digital camera.

The step of identification by section and plate can comprise an analysis of the groups of filaments, to deduce a classification among at least the following types: single multifilament, multicore multifilament, multicore multicore sheath, single-sheath multi-core. You can then consult a web-page reference base of sections and determine the section which most closely resembles the plate obtained just before. This process can advantageously be supported by a smartphone application.

Alternatively, the identification step is to take a reference written on the cord itself. The product identification sheet is then consulted on a web page and the type of filamentous structure and coating is found there.

Alternatively, the identification step is to identify a mark representative of the manufacturer of the string strand.

According to yet another embodiment, the color or colors present on the outer sheath of the string strand can be used to determine the type of string, which forms another method for identification step S0.

According to yet another embodiment, both a mark representative of the manufacturer and a color representative of the type of string strand are recorded to conclude an identification of the type of string strands to be recycled (step S0).

After identification, the process involves selecting one or more steps below in order to separate the string strand into components or small individual pieces.

Preferably, the step of collecting used strings will support the use of recovery bins, in particular selective bins, each designed to receive a particular type of string.

S1—Mechanical Separation Step

FIG. 3 illustrates a peeling step and/or a step of grinding the string strand. When the length of the string strand to be processed allows it, the string strand can be passed through a machine similar to an extruder 36 shown in FIG. 3.

In this machine 36, rasps mounted on rollers 37 are sandwiched together and, using the rotary movement of the rollers, the rasps peel the coating material from at least the outer edge of the section of the string strand. The heart 21 of the string is under tension and comes out of the machine without the outer edge coating 22, which is collected in a container at the outlet of the peeling machine 36. The arrangement is horizontal in the example illustrated. There can be several rasps in series (several passes of peeling).

As for the grinding step, the latter allows the string strand to be cut into small pieces which can then be treated by a chemical, thermal or biological separation step. For this, as illustrated in FIG. 4, a crusher 44 comprises a hopper 46 into which pieces of string strand are poured. Two (or more) counter-rotating rollers 47, by virtue of a plurality of surface teeth, shred the string strand. At the low side exit, small unit elements 48 collect in a container.

S2—Chemical Separation Step

In this case, a solvent is used to completely and reliably separate the technical fibers from the coating material. You can use trichlorethylene, trichloroethane, dichloromethane, tetrachloroethane, acetone, etc . . . .

FIG. 5 illustrates dissolution equipment comprising a tank 53 filled with a solution with the aforementioned solvent 54. String strands 55 are immersed therein, without any particular constraint on their length (short strands, long strands).

After a predetermined time, the action of the solvent solution is considered sufficient and the resulting solution is sieved, the fibers are retained by the sieve and the coating material dissolved in the solvent solution passes through.

S3—Thermal Separation Step

Figures 6, 7:
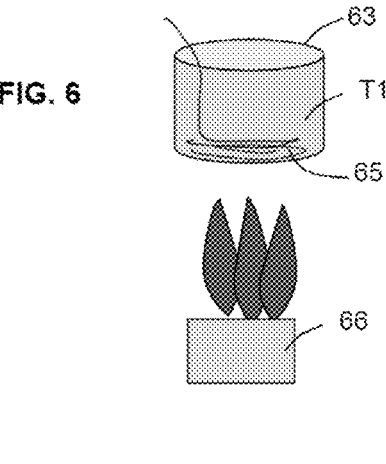
FIG. 6 illustrates a thermal separation step.
FIG. 7 illustrates a biological separation step.

FIG. 6 illustrates a piece of equipment with a vapo-thermolysis step, with heating of the string strand above 150°. Here, stationary equipment has been shown, but an embodiment with progressive displacement is also provided.

Depending on the melting points of the different components, the constituents are gradually separated by increasing the temperature. The components that have the lowest melting point are recovered first and the components that have the highest melting point, last.

In the example shown, the string strand 65 is placed, without any particular constraint on its length (short strands, long strands), in an oven 63 and then heated to a first predetermined temperature T1, for example 160° C., in order to melt one of the constituents of the cord. Heating 66 can be done by different means, a burner, infra-red lamp rails, an induction furnace, etc. . . .

The molten part is then extracted and the remainder is separated.

Of course, it is possible to repeat the operation described above with a second predetermined temperature T2, for example 220° C. in order to melt another component of the cord which is then separated as a melted part.

According to an example, in the logic of increasing temperatures, we can first separate the polyolefins, then the polyesters, then the polyurethanes, then the polyamides, etc. Carbon and titanium fibers are the last remaining components.

S4—Biological Separation Step

The biological separation step involves extended contact of the string strands with active biological agents including microalgae and/or enzymes.

Thus, certain components of interest in rope strands are degraded by said active biological agents. It is noted that, even if the time required is longer, this solution is the most economical in energy in achieving the separation of the components.

Furthermore, such a biological separation step is also used to process natural gut strings for recycling. Active biological agents comprising microalgae and/or enzymes degrade natural gut strings into elementary chemical components which then no longer have any negative impact on the environment.

FIG. 7 illustrates dissolution equipment comprising a tank 73 filled with a solution with greedy enzymes 74 and/or microalgae. String threads 75 are immersed therein, without any particular constraint on their length (short strands, long strands).

After a predetermined time, the action of the greedy enzymes and/or microalgae is considered sufficient and the resulting solution is sieved, the fibers are retained by the sieve and the coating material dissolved in solution passes through.

Recovery of Separated Constituents

In addition, there is a step for upgrading the products/components from one of the steps /S1/ to /S4/.

The recovery step includes, for example, the incorporation of the components into new strings, and/or into technical clothing with padding, and/or into technical protective clothing, and/or into flame retardant technical clothing.

The recovery step can include energy recovery, whereby one or more residues from the aforementioned separation step are burned.

Other Considerations

It should be noted that the different steps and solutions for the identification, separation and recovery steps are applicable, mutatis mutandis, to types of strings other than tennis strings, in particular the technical strings used for sailing, rock climbing, mountaineering or other sports, as well as the strings of stringed musical instruments.

What is claimed is:

1. A method of recycling composite strings, the composite strings each having at least one filament, the method comprising:

a step of identifying (S0) a type of the composite strings including making a cross-section, taking a photo with magnification, and analyzing groups of the at least one filament to deduce therefrom a classification, and at least one step of separating components comprising one or the other of the following steps /S1/, S2/, /S3/, /S4/ as defined below:

/S1/ a mechanical separation step,

/S2/—a chemical separation step,

/S3/—a thermal separation step,

/S4/—a biological separation step.

2. The method according to claim 1, wherein the composite further comprise a coating.

3. The method according to claim 1 wherein the at least one filament comprises a synthetic fiber.

4. The method according to claim 1, wherein the at least one filament comprises an assembly of structural fibers.

5. The method according to claim 1, wherein according to the step of mechanical separation (/S1/) there is provided at least one of a peeling step and a grinding step.

6. The method according to claim 2, wherein the coating comprises polyurethane and/or an elastomer, the chemical separation step (/S2/) comprises dissolving the coating in a solvent.

7. The method according to claim 1, wherein the thermal separation step (/S3/) comprises a vapor-thermolysis step, with heating of the composite strings beyond 150° C.

8. The method according to claim 1, wherein the step of biological separation (/S4/) comprises extended contact of the composite strings with active biological agents comprising microalgae and/or enzymes, so that selected components are degraded by the active biological agents.

9. The method according to claim 1, wherein the deduced classification is selected from at least one of the following types: single multifilament, multicore multifilament, multi-core multi-sheath, and multi-core single-sheath.

10. The method according to claim 1 further comprising a step of upgrading products/components resulting from one of the steps /S1/ to /S4/, the upgrading step comprising incorporation of the products/components into at least one selected from the group consisting of new strings, technical clothing with padding, technical protective clothing, and flame retardant technical clothing.

11. The method of claim 1, including energy upgrading wherein one or more residues from separation of the at least one filament and the coating can be burned.

12. The method of claim 3 wherein the synthetic fiber is at least one fiber chosen from aramid fiber, polyester fiber, polyimide fiber, polyolefin fiber, polyurethane fiber, elastomer fiber, and carbon fiber.

13. The method of claim 1 wherein the at least one filament comprises a metal fiber.

14. The method of claim 13, wherein the metal fiber comprises titanium.

15. A method of recycling composite strings having at least one filament and a coating, the coating comprising polyurethane and/or an elastomer, the method comprising:

identifying a type of the at least one filament by making a cross-section, taking a photo with magnification, and analyzing a group of the least one filament;

separating the composite strings and the coating;

dissolving the coating in a solvent; and incorporating the separated composite strings into at least one selected from the group consisting of new strings, technical clothing with padding, technical protective clothing, and flame retardant technical clothing.

16. The method of claim 15, wherein a peeling step is provided to separate the coating from at least an outer edge of a section of the composite strings.

17. The method of claim 15, wherein a grinding step is provided to separate and cut the composite strings into smaller pieces.

18. The method of claim 15, including a step of heating the composite strings beyond 150° C. to separate any one of the at least one filament and the coating.

19. The method of claim 15, including extended contact of the composite strings with active biological agents comprising microalgae and/or enzymes so that selected components in the composite strings are degraded by the active biological agents.

20. The method of claim 15, including energy upgrading wherein one or more residues from separation of the at least one filament and the coating can be burned.

* * * * *